United States Patent [19]

Gudkin et al.

[11] Patent Number: 4,519,389
[45] Date of Patent: May 28, 1985

[54] THERMOELECTRIC CRYOPROBE

[76] Inventors: Timofei S. Gudkin, ulitsa Dibenko, 23, korpus 5, kv. 92; Evgeny K. Iordanishvili, prospekt Morisa Toreza, 40, korpus 4, kv. 35, both of Leningrad; Nikolai S. Lidorenko, ulitsa Kibalchicha, 2, korpus 1, kv. 217, Moscow; Bella E. Malkovich, prospekt Morisa Toreza, 102, korpus 2, kv. 13; Mikhail I. Razumovsky, prospekt Smirnova, 71, kv. 15, both of Leningrad; Igor B. Rubashov, ulitsa Novo-Alexeevskaya, 1, kv. 151, Moscow, all of U.S.S.R.

[21] Appl. No.: 442,223
[22] PCT Filed: Mar. 23, 1981
[86] PCT No.: PCT/SU81/00028
§ 371 Date: Nov. 8, 1982
§ 102(e) Date: Nov. 8, 1982
[87] PCT Pub. No.: WO82/03169
PCT Pub. Date: Sep. 30, 1982

[51] Int. Cl.³ ............................... A61B 17/36
[52] U.S. Cl. .................... 128/303.1; 62/3; 62/293
[58] Field of Search .......... 128/303.1, 399, 742; 62/3, 293; 433/32

[56] References Cited

U.S. PATENT DOCUMENTS

| 3,249,469 | 5/1966 | Stegherr | 62/3 X |
| 3,971,229 | 7/1976 | Privas | 62/3 |
| 4,308,013 | 12/1981 | Major | 128/742 X |

Primary Examiner—Lee S. Cohen
Attorney, Agent, or Firm—McAulay, Fields, Fisher, Goldstein & Nissen

[57] ABSTRACT

A thermoelectric cryoprobe comprising a handle composed of two electrically insulated halves made of a material possessing high heat conduction. One end of the handle is tapered, and a semiconductor cooling thermoelement is arranged at the butt of the tapered end. The height of the thermoelement does not exceed the radius thereof. The surface of a commutation plate of the thermoelement is the working surface of the thermoelectric cryoprobe.

20 Claims, 3 Drawing Figures

U.S. Patent
May 28, 1985
4,519,389
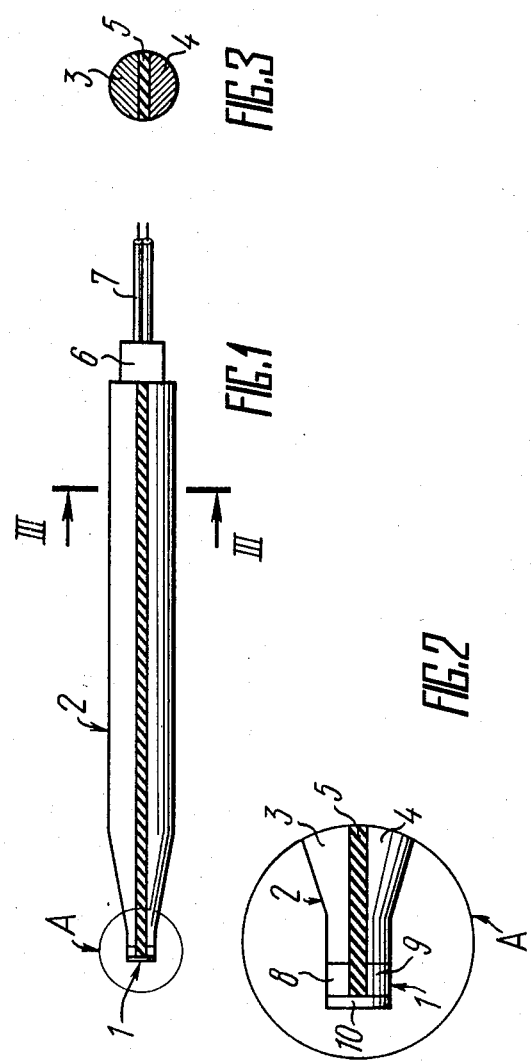

THERMOELECTRIC CRYOPROBE

FIELD OF THE INVENTION

This invention relates to thermoelectric refrigerating plants and, in particular, to thermoelectric cryoprobes.

BACKGROUND ART

In modern practice the most popular medical cryoprobes make use of gaseous or liquid refrigerants (carbon dioxide, freons, liquid nitrogen and others) which can be divided into two basic types, according to the method of refrigerant supply, namely cryoprobes with discrete and continuous types of supply.

Cryoprobes of the first type are basically reservoirs filled with liquid refrigerants in advance to cool a metal rod. The latter is in fact the probe. The temperature of the cryoprobe tip cannot, therefore, be controlled in any way in the course of an operation and is relatively low (about −40° C.).

The probe can be warmed up in case of a dangerous development in the operation (deep freezing, freezing of surrounding tissue, etc.) by means of a warm sterile liquid fed directly to the freezing area.

The process of warming up is lengthy (tens of seconds) and reapplication of the cryoprobe in the operation required refilling of the refrigerant.

The above mentioned unfavourable developments are even more frequent since the cryoprobe is introduced into the operation field already cooled, as well as due to the fact that the probe tip has cooled side surfaces.

Cryoprobes using continuously supplied refrigerant are much more efficient, but, consequently, more complicated. In this case use is made of complex gas apparatuses, maintenance becomes quite a problem, as well as preparation of the cryoprobe for an operation. A great reserve of refrigerant is a necessity.

A new medically oriented cryoprobe based on the Peltier effect method of thermoelectric cooling was proposed in the 60's (cf., for example, I. K. Poltinnikova, E. A. Kolenko, Intracapsular Extraction of a Cataract by Semiconductor Device. Ophthalmological Magazine, No. 8, 1964, pp.563–566. in Russian).

The medical thermoelectric cryoprobe comprises a semiconductor cooling thermoelement and a double handle. The p and n branches of the thermoelement are mounted on the two halves of the handle.

Refrigerating power of the thermoelement is concentrated on the functional surface of the cryoprobe which is in fact a metal concentrator-tip placed on the switching plate of the thermoelement. The specific refrigeration effect of the functional cryoprobe surface required for freezing is attained in this manner.

Heat sink from the hot junctions of such thermoelements in cryoprobes is effected with the help of running water circulating inside the handle. The masive concentrator-tip determines in this case great thermal inertia of the cryoprobe. For cooling such a cryoprobe should be cut in 3 minutes before freezing the tissue. It is, therefore, still necessary to introduce a pre-cooled probe into the operation field, its side cooled surfaces being large as compared to the functional working surface.

As it has already been mentioned these features are liable to produce dangerous developments in operations, particularly in ophthalmological operations where the field of operation is very small.

Moreover, in such conditions water cooling hoses feeding water to the cryoprobe handle make it very hard to manipulate the cryoprobe.

DISCLOSURE OF THE INVENTION

The invention resides in providing a miniature, quick response thermoelectric cryoprobe which is electronically cooled by means of a new thermal circuit.

This object is achieved in that in a thermoelectrical cryoprobe comprising a semiconductor cooling element and a handle made up of two electrically separated parts, according to the invention, one end of the handle is narrowed and the butt end thereof carries a semiconductor cooling thermoelement whose height does not exceed the radius thereof, the surface of the switching plate of said thermoelement being the working surface of the cryoprobe, the two parts of the handle being made of a material possessing high heat conduction.

The proposed thermoelectric cryoprobe offers the following useful features.

Low thermal inertia. The minimum temperature of the working surface is attained in 1–8 seconds after the cryoprobe is switched on. The cryoprobe can be introduced into the operation field while still warm and attain the working temperature practically instantly after being applied to a spot most suitable for freezing.

Cooling is localized on the working surface of the cryoprobe, there are no side surfaces which can freeze up the surrounding tissue.

The cryoprobe can be defreezed from the tissue in 1 or 2 seconds counting from the moment the probe is switched out. The cryoprobe is then ready for a repeated cryaction cycle.

The cryoprobe is connected to external devices by means of a thin electric cable which in no way hinders the surgeon's movements.

These advantages sharply decrease probability of unfavourable developments during an operation and permit modern methods of multiple applications of the cryoprobe.

Extreme ease of maintenaince and preparation for operations of the cryoprobe is another important advantage of the proposed invention.

BRIEF DESCRIPTION OF THE DRAWINGS

The invention will now be described in greater detail with reference to a specific embodiment thereof, taken in conjunction with the accompanying drawings, wherein:

FIG. 1 illustrates a general view of a thermoelectric cryoprobe, according to the invention;

FIG. 2 illustrates an enlarged view of a part of a handle of a thermoelectric cryoprobe equipped with a thermoelement;

FIG. 3 illustrates a view taken along line III—III of FIG. 1, according to the invention.

BEST MODE FOR CARRYING OUT THE INVENTION

The proposed thermoelectric cryoprobe comprises, in accordance with the invention, a semiconductor thermoelement 1 (FIG. 1) mounted on a butt of a narrowing end of a handle 2.

The handle 2 has two halves 3 and 4 (FIG. 2) which are metal half-cylinders secured together with a dielectric gasket 5 inseted therebetween. The butt end of the handle 2 opposite to the semiconductor thermoelement 1 (FIG. 1) has an electric connector 6 coupling the parts 3 and 4 of the handle to the current carrying wires of a two-core electric cable 7. The parts 3 and 4 of the handle 2, according to the invention, are made of a material possessing high heat conduction, of copper, for example.

The semiconductor thermoelement 1 comprises two semiwashers 8 and 9 (FIG. 2) made of known thermoelectric materials based on bismuth and antimony tellurides.

The semi-washers 8 and 9 are connected by a silver commutation plate 10 whose thickness does not exceed 0.1 mm. The commutation plate 10 forms the cold junction of the semiconductor thermoelement 1 and its functional surface is the working surface of the cryoprobe.

Hot butt ends of the semi-washers 8 and 9 of the thermoelement 1 are soldered directly on the butt ends of the parts 3 and 4 of the handle 2 and are in good electrical and thermal contact therewith, thus forming hot junctions of the semiconductor thermoelement 1.

The surfaces of the handle 2 are chrome plated in order to protect them from the sterilizing solutions. The side surfaces of the semiconductor thermoelement 1 are coated by an epoxy resin film.

A medical thermoelectric cryoprobe for cryoextraction of a lens has a semiconductor thermoelement whose diameter does not exceed 2 mm. The height of the semiconductor thermoelement 1 in this case is not more than 1 mm.

The thermoelectric cryoprobe operates as follows. Electric current is fed from a rectifier or some other DC power source (not shown) via the cable 7 (FIG. 1) and the connector 6, to the parts 3 and 4 (FIG. 2) of the handle 2, the semi-washers 8 and 9 and the commutation plate 10 of the semiconductor thermoelement 1. The commutation plate 10 is therefore cooled. The voltage supplied to the parts 3 and 4 of the handle 2 is about 0.1 volts, current intensity is about 10 a.

It is common knowledge that the specific refrigerating power of the semiconductor thermoelement 1 (the refrigerating effect of a unit of area of the cold junction) grows with the decrease of the height thereof. With the height of the semiconductor thermoelement 1 limited in accordance with the invention, the commutation plate 10 alone, without a concentrator tip, sufficient for freezing up the lens of the eye.

Thus the commutation plate 10 becomes the working organ of the cryoprobe and the thermal lag of the thermoelectric cryoprobe depends upon the thermal inertia of the thermoelement 1 alone. In other words, the time required for the thermoelectric cryoprobe to attain its working temperature coincides with the time required for the semiconductor thermoelement 1 to attain its stationary working temperature.

This temperature is in inverse proportion to the height of the semiconductor thermoelement. With the height of the semiconductor thermoelement 1 limited in accordance with the invention, the stationary working temperature thereof is reached in one to two seconds after current is turned on thus ensuring a short thermal lag of the cryoprobe.

Heat liberated by hot junctions of the semiconductor thermoelement 1 flows via the tapered portion of the handle 2 and is further partially accumulated by this handle 2 and partially dissipated.

Reliable heat removal from the hot junction is also facilitated by the material of the parts 3 and 4 of the handle 2, possessing high thermal conduction, copper, in particular, which is one of the forerunners among metals as far as heat conduction is concerned.

Some heat liberated by the semiconductor thermoelement 1 is accumulated by the handle 2 in quasistationary conditions where the temperature of the hot junction varies. But such variations prove insignificant and lead to no substantial change in the temperature of the commutation plate 10, which is in contact with the cooled tissue, even during periods many times over the time required for lens extraction.

The thermoelectric cryoprobe is warmed up and defreezed from tissue when current is cut off. Heat flows to the freezed-up tissue from the handle 2 via the thermoelement 1 whose height is limited so intensively that the tissue is released in 1 or 2 seconds after current is cut off.

Numerous clinical experiments with the thermoelectric cryoprobe have demonstrated that it is very effective in cataract removal operations, in some brain operations and other instances where medium-temperature (not more than −20° C.) local cooling of tissues is required for reliable surface freeze-up.

INDUSTRIAL APPLICABILITY

The invention can used in manufacturing miniature cryoprobes in medicine and, in particular, for ophthalmological operations.

We claim:

1. A thermoelectric cryoprobe, comprising:
   a handle comprising two electrically separated longitudinal half-cylinders made of a high heat conduction material;
   a semiconductor cooling thermoelement having a hot junction in contact with said two half-cylinders, said thermoelement including a commutation plate mounted on one end of said handle and in direct contact with the latter by said hot junction, the height of said thermoelement does not exceed its radius, and said commutation plate having a functional surface which is a working surface of said thermoelectric cryoprobe;
   a heat sink for removal of heat from said semiconductor cooling thermoelement, said heat sink comprising said two electrically separated longitudinal half-cylinders forming part of said handle; and
   means for feeding current to the longitudinal half-cylinders of said handle.

2. The probe of claim 1, wherein one of the ends of said handle is tapered.

3. The probe of claim 2, wherein said semiconductor cooling thermoelement is mounted on said tapered end.

4. The probe of claim 3, wherein said commutation plate has a thickness not exceeding 0.1 mm and forms the cold junction of said semiconductor thermoelement.

5. The probe of claim 1, including a dielectric gasket between said two half-cylinders.

6. The probe of claim 1, wherein said current feeding means includes an electrical connector connecting said two half-cylinders to a two core electrical cable.

7. The probe of claim 1, wherein said semiconductor thermoelement comprises two semi-washers connected to and by said commutation plate.

8. The probe of claim 7, wherein said commutation plate has a thickness not exceeding 0.1 mm.

9. The probe of claim 7, wherein said two electrically separated half-cylinders each have a butt end, and said semi-washers are soldered directly onto said butt ends to form hot junctions of said semiconductor thermoelement.

10. The probe of claim 9, wherein the surface of said handle is chrome-plated.

11. The probe of claim 1, wherein said thermoelement has a diameter not exceeding 2 mm.

12. The probe of claim 1, wherein the height of said thermoelement does not exceed 1 mm.

13. The probe of claim 1, wherein said commutation plate has a thickness not exceeding 0.1 mm.

14. A thermoelectric cryoprobe, comprising:
a handle including two electrically separated longitudinal metal half-cylinders each made of a high heat conduction material;
one end of said handle being tapered;
a semiconductor cooling thermoelement having a hot junction and including a commutation plate mounted on said tapered end of said handle and in direct contact therewith by said hot junction, the height of said thermoelement does not exceed its radius, said hot junction being in contact with said two half-cylinders, and said commutation plate having a functional surface which is a working surface of said thermoelectric cryoprobe;
a heat sink for removal of heat from said semiconductor cooling thermoelement, said heat sink including and being formed from said two electrically separated half-cylinders forming part of said handle; and
means for feeding current to the longitudinal half-cylinders of said handle.

15. The probe of claim 14, including a dielectric gasket between said two metal half-cylinders.

16. The probe of claim 15, wherein said current feeding means includes an electrical connector connecting said two metal half-cylinders to a two core electrical cable.

17. The probe of claim 16, wherein said semiconductor thermoelement comprises two semi-washers connected to and by said commutation plate.

18. The probe of claim 17, wherein said semi-washers are soldered directly onto butt ends of said two electrically separated half-cylinders to form hot junctions of said semi-conductor thermoelement.

19. The probe of claim 18, wherein said commutation plate has a thickness not exceeding 0.1 mm and forms the cold junction of said semiconductor thermoelement.

20. The probe of claim 19, wherein said thermoelement has a diameter not exceeding 2 mm and a height not exceeding 1 mm.

* * * * *